United States Patent [19]

Zibelin

[11] Patent Number: 4,600,405
[45] Date of Patent: Jul. 15, 1986

[54] MECHANICAL HEART

[76] Inventor: Henry S. Zibelin, 1423 26th St., NW., Winter Haven, Fla. 33881

[21] Appl. No.: 784,730

[22] Filed: Oct. 7, 1985

[51] Int. Cl.$^4$ .............................................. A61F 2/22
[52] U.S. Cl. ................................................... 623/3
[58] Field of Search ........................ 623/3; 128/1 D; 417/481, 482, 410, 417, 418

[56] References Cited

U.S. PATENT DOCUMENTS

| 23,094 | 3/1859 | Lawrence et al. | 417/482 |
|---|---|---|---|
| 3,720,485 | 3/1973 | Holman | 623/3 |
| 3,733,616 | 5/1973 | Willis | 623/3 |
| 3,827,833 | 8/1974 | Jinkawa | 417/482 |
| 3,874,002 | 4/1975 | Kurpanek | 623/3 |
| 4,014,318 | 3/1977 | Dockum et al. | 623/3 |
| 4,102,610 | 7/1978 | Taboada | 417/417 |
| 4,210,409 | 7/1980 | Child | 417/417 |
| 4,221,548 | 9/1980 | Child | 623/3 |
| 4,302,854 | 12/1981 | Runge | 623/3 |
| 4,310,930 | 1/1982 | Goldowsky | 417/481 |
| 4,375,941 | 3/1983 | Child | 623/3 |
| 4,512,726 | 4/1985 | Strimling | 623/3 |

Primary Examiner—Richard J. Apley
Assistant Examiner—James Prizant
Attorney, Agent, or Firm—William M. Hobby, III

[57] ABSTRACT

The present invention relates to an artificial heart for pumping blood through a circulatory system and includes an artificial heart housing having a plurality of expandable and contractable chambers formed therein and an oscillating impeller located in the housing and attached to the housing for expanding and contracting each chamber formed therein. The oscillating impeller is driven electromechanically from the outside of the housing. A plurality of inlets and outlets allow the blood to be pumped to and from the different parts of the body.

16 Claims, 17 Drawing Figures

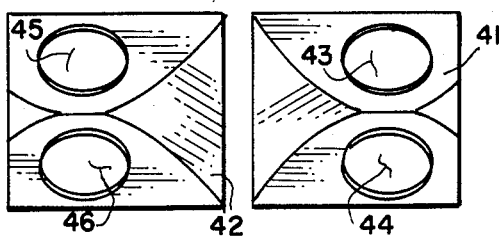
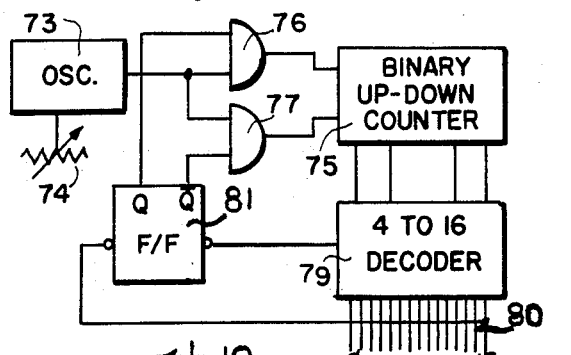
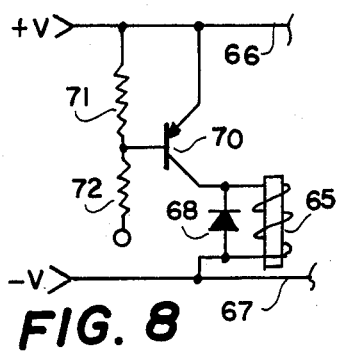
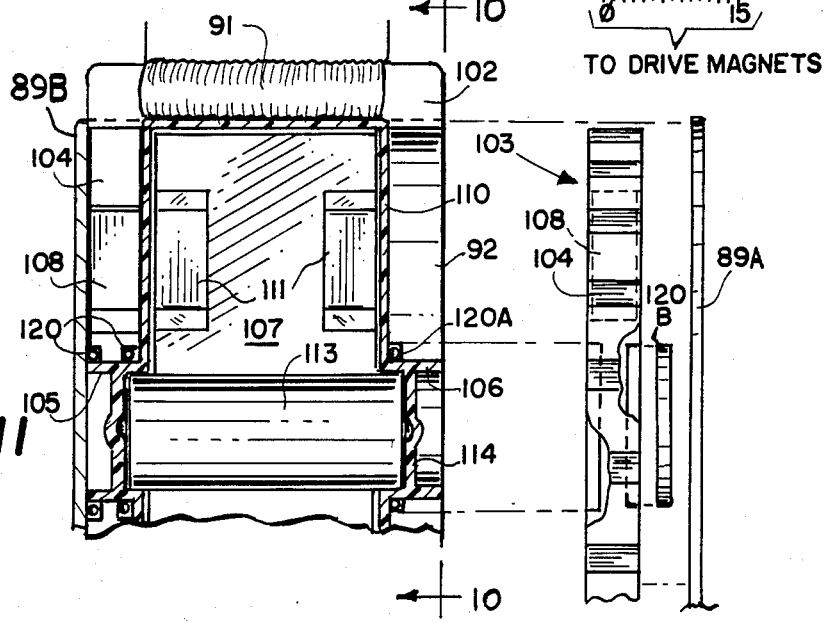
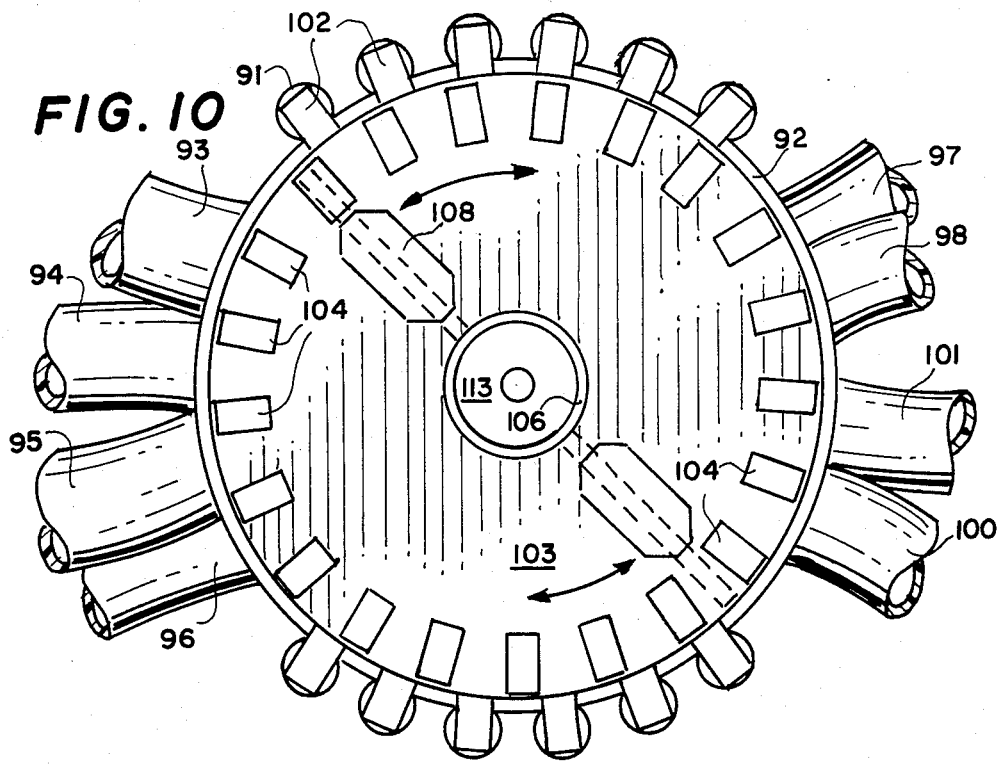

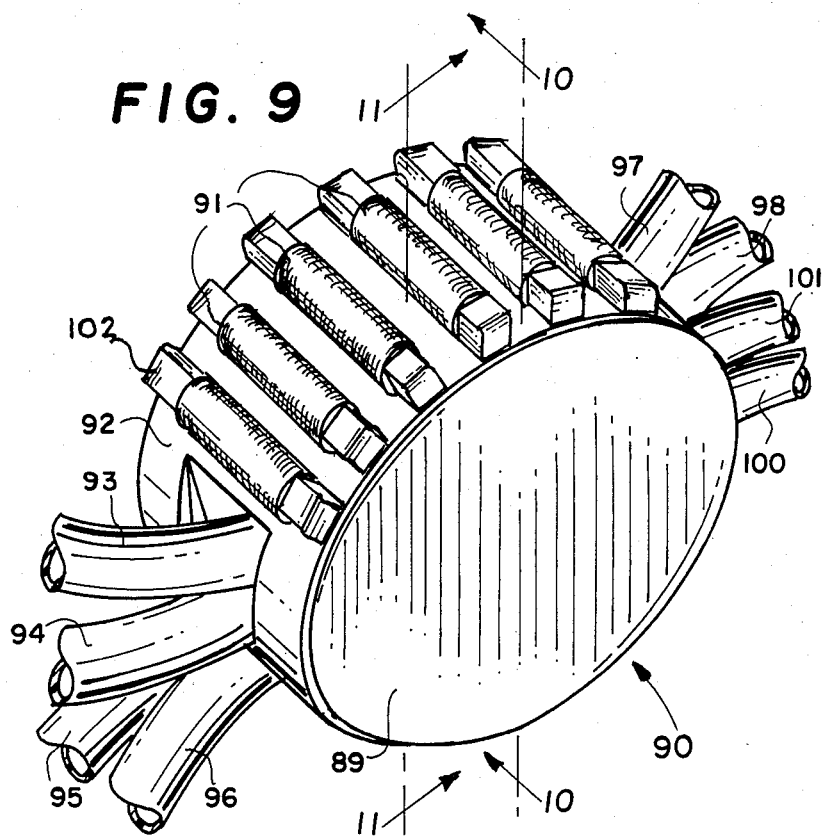
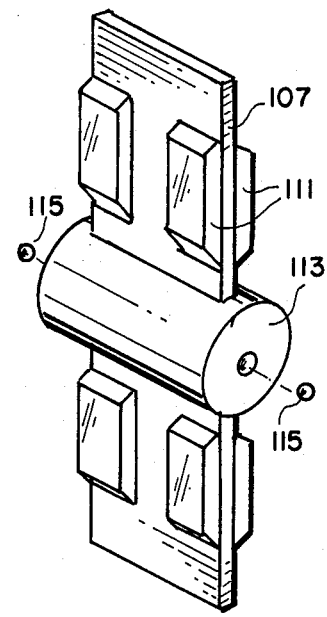
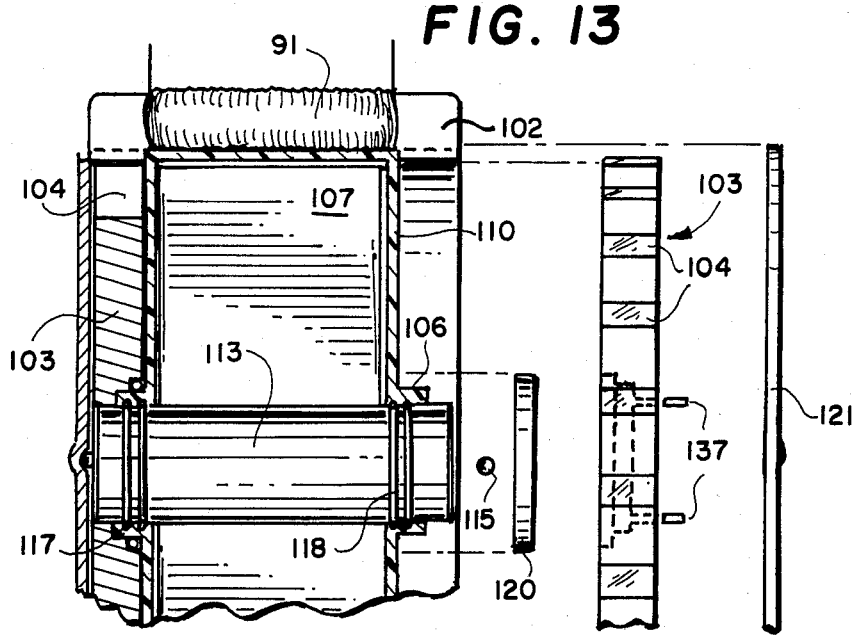

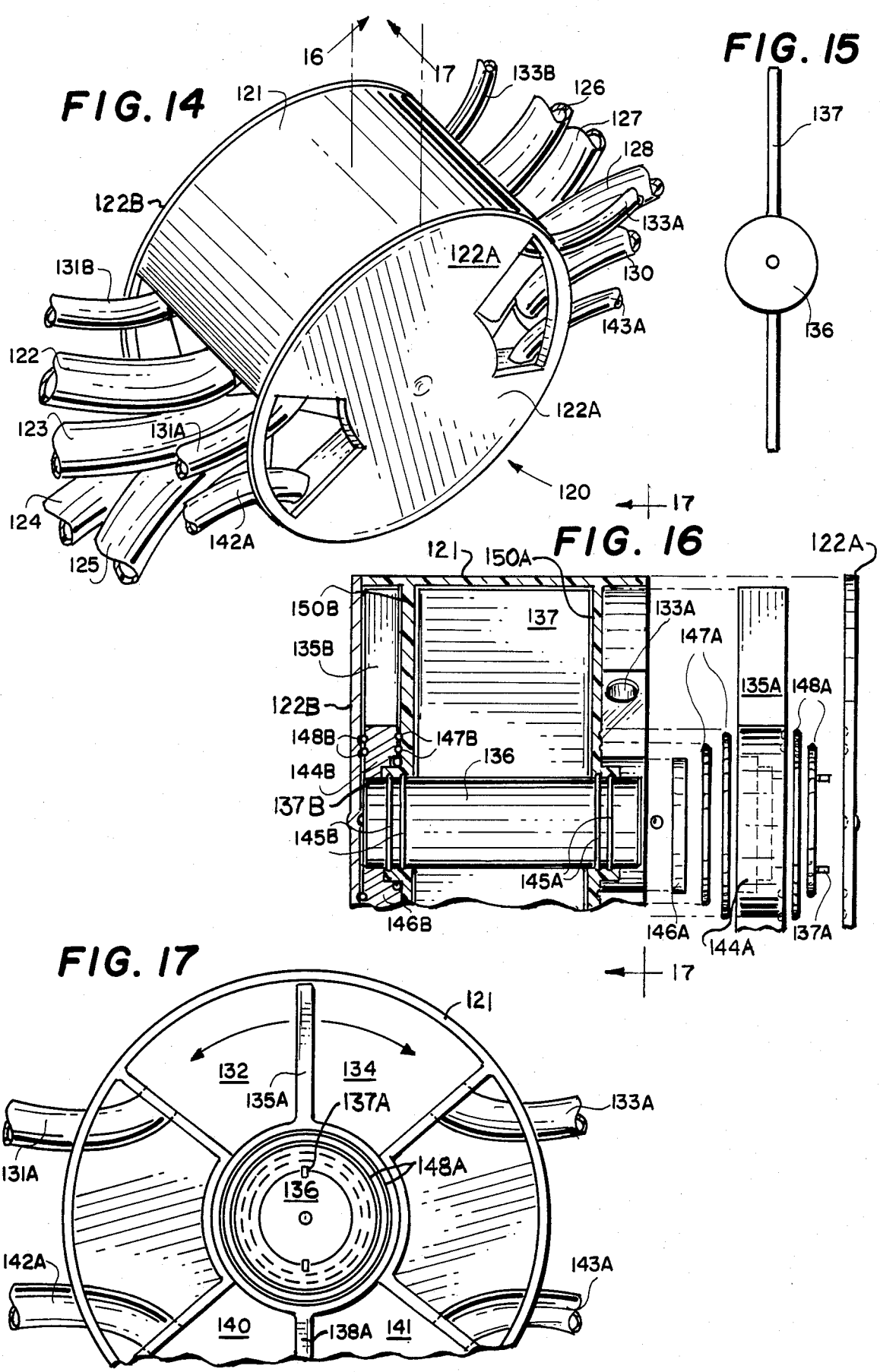

MECHANICAL HEART

BACKGROUND OF THE INVENTION

The present invention relates to an artificial heart for pumping blood through a circulatory system, and especially to such a system using an electromagnetic actuation of an impeller located in a housing.

In the past there have been a great variety of suggestions for implanting an artificial heart into a living human body, and this has presented any number of problems. The main problem has been in the design and construction of an actual pumping unit and drive system for the artificial heart. Many suggestions have been made for drive units, and these include devices powered by atomic energy, as well as piezoelectric devices and pumping units driven by electric motors. Electric motor driven pumps may include valve operating pumps, oscillating pumps, rotary pumps, or the like. There have also been electromagnetically driven pumps which generally have a coil wrapped around a core which is connected to a diaphragm for pumping the diaphragm to act as a flexible ventricle.

Finally, it has been suggested to make artificial hearts having pumping units powered by compressed gas and these can be used to compress diaphragms as well as bag-type artificial hearts in which a flexible polymer bag is enclosed within a rigid container so that compressed air can squeeze the flexible bag to cause the pumping action. Prior U.S. patents which show artificial hearts include the Willis Jr., patent for an Electromagnetically Actuated Artificial Heart, U.S. Pat. No. 3,733,616 and the Kurpanek, U.S. Pat. No. 3,874,002 for a Pulsatile Magneto-motive Artificial Heart. The Dockum, et al, U.S. Pat. No. 4,014,318 shows a Circulatory Assist Device and System, while the Holman Jr., U.S. Pat. No. 3,720,485 shows an Artificial Heart actuated with electromagnetic solenoids. The Runge, U.S. Pat. No. 4,302,854 shows an Electrically Activated Vascular Shunt or Left Ventricular Assist while Goldowsky, U.S. Pat. No. 4,310,930 shows a Rigid Vane Artificial Heart, U.S. Pat. No. 4,375,941 to Child shows a Method and Apparatus for pumping blood. In addition to these patents, there have been a number of suggestions for use in pumping various types of liquids with oscillating pumps such as shown in the Lawrence and Safley U.S. Pat. No. 23,094 for an Oscillating Pump and in U.S. Pat. No. 3,827,833 to Jinkawa for a Rotor Cooling Device in an Oscillating Type Compressor. Other patents may be seen in Child U.S. Pat. Nos. 4,221,548 and 4,210,409 for a Dual Action Solenoid Pump and in the Taboada, et al, U.S. Pat. No. 4,102,610 for a Constant Volume Seal-free Reciprocating Pump.

The present invention deals with one basic principle for an artificial heart, with different power sources to drive the heart. An electromagnetic drive unit is connected to a diaphragm or to a finger pump and operates on an oscillating pump oscillating an impeller in a sealed housing. The impeller may have a permanent magnet on the armature rotor driven by a series of stator coils producing an electric field in accordance with an electric drive circuit. The single impeller can be utilized to actuate four separate chambers in a housing.

SUMMARY OF THE INVENTION

An artificial heart for pumping blood through a circulatory system includes a housing having a plurality of expandable and contracting chambers formed therein, and one oscillating impeller located in the housing and dividing two chambers in the housing into four chambers. The oscillating impeller can be oscillated electromagnetically to expand and contract all four chambers simultaneously responsive to the back-and-forth rotary movement of the impeller. The impeller is rotably mounted in the housing and acts as an armature or rotor and may have permanent magnet members on top and bottom and each end of the impeller which are actuated by the stator electric field which is generated through a plurality of stator windings around the housing or casing which are sequentially actuated by an electronic circuit. The housing has a plurality of inlets and outlets, including at least one inlet and one outlet for each chamber, with each inlet and outlet having a check valve to control the flow into and from the chamber.

BRIEF DESCRIPTION OF THE DRAWINGS

Other objects, features and advantages of the present invention will be apparent from the written description and the drawings in which:

FIG. 6 is an elevational view of the housing for valve inlets and outlets of the artificial heart of FIGS. 1 thru 5;

FIG. 7 is a block diagram of an electrical circuit for driving the artificial heart of FIGS. 1 thru 6;

FIG. 8 is a schematic diagram of a typical magnetic driver circuit;

FIG. 9 is a perspective of an alternate embodiment of an artificial heart in accordance with the present invention;

FIG. 10 is a sectional view taken on line 10—10 of FIGS. 9 and 11;

FIG. 11 is a sectional view taken on line 11 of FIG. 9;

FIG. 12 is a perspective view of a rotor for use in the embodiment of FIGS. 9 thru 11;

FIG. 13 is an exploded sectional view of half of the heart pump of FIG. 9 with internal variations;

FIG. 14 is a perspective view of another embodiment of an artificial heart in accordance with the present invention;

FIG. 15 is a side elevation of a rotor impeller for use in the heart pump of FIGS. 14, 16, & 17;

FIG. 16 is an exploded sectional view taken on line 16 of FIG. 14; and

FIG. 17 is a sectional view taken on line 17 of FIG. 14 & 16.

DESCRIPTION OF THE PREFERRED EMBODIMENT

Figure 1:
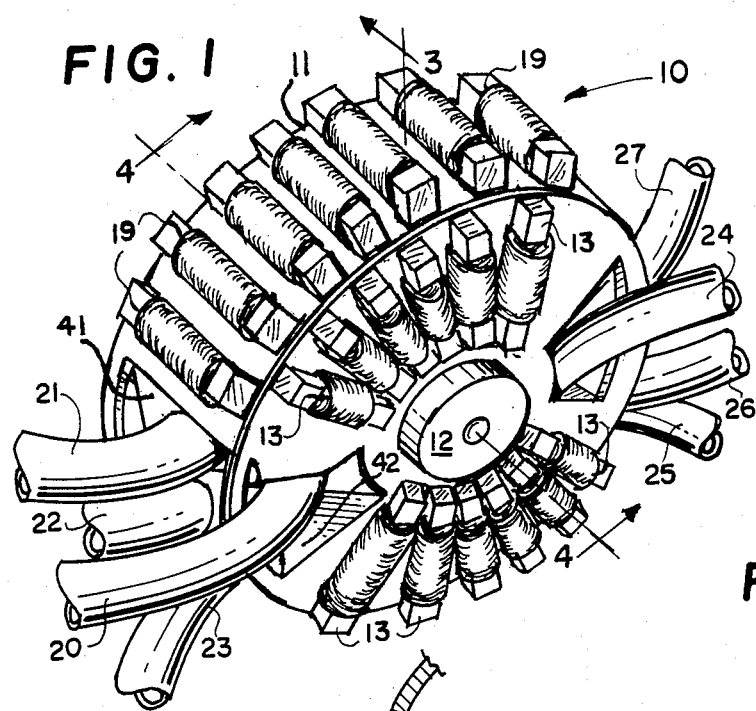
FIG. 1 is a perspective view of a preferred embodiment of an artificial heart in accordance with the present invention.
Figure 2:
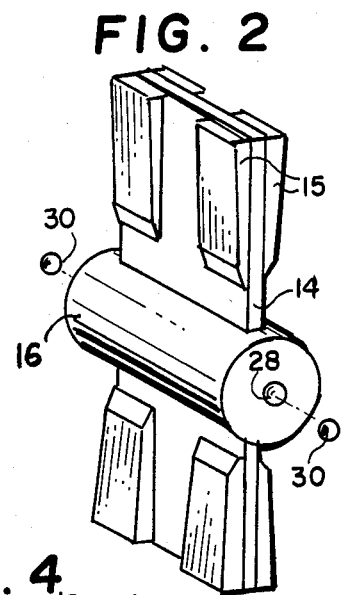
FIG. 2 is a perspective view of the rotary impeller for the artificial heart of FIG. 1.
Figure 5:
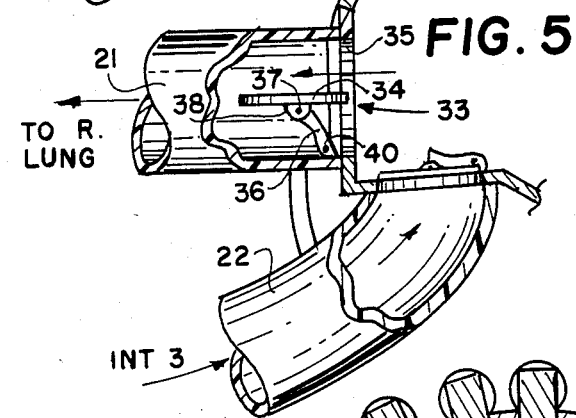
FIG. 5 is a sectional view of a pair of valve elements of the artificial heart of FIGS. 1 thru 4.
Figure 3:
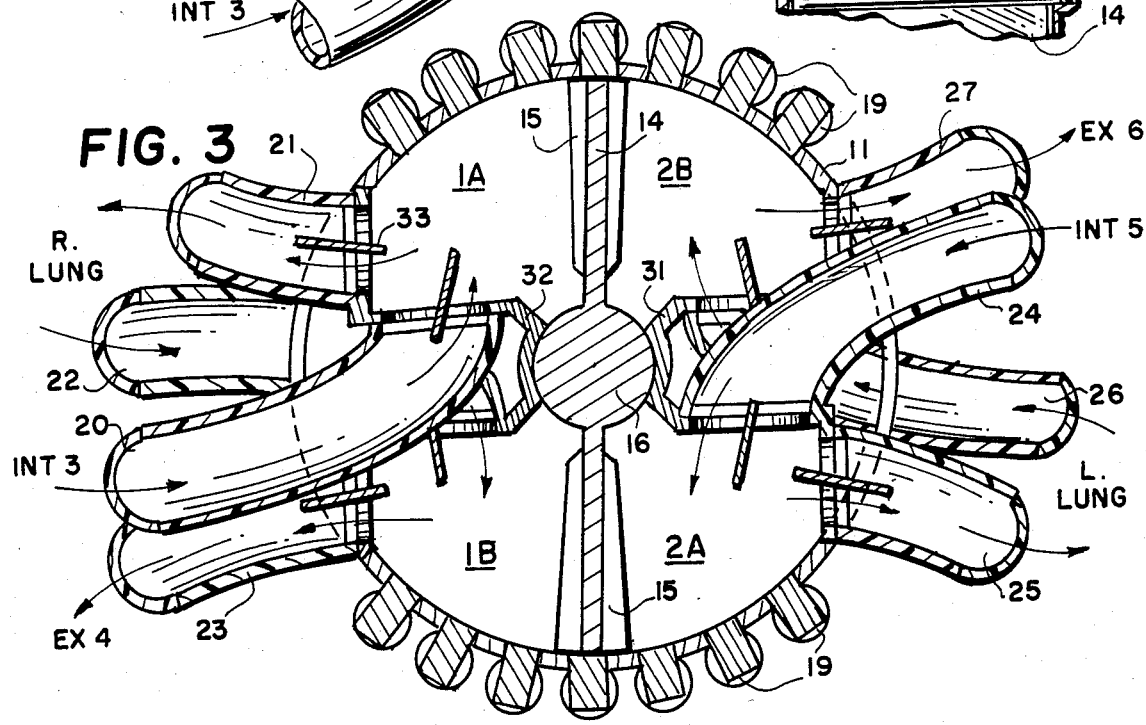
FIG. 3 is a sectional view taken on line 3—3 of FIG. 1.

Referring to the drawings and especially to FIG. 1 thru 6, and artificial heart 10 is shown having a housing or casing 11 which has a bearing support cup portion 12 protruding from both sides. The non-magnetic housing 11 may be made of a polymer material and has a generally cylindrical shape and has a plurality of stator windings 13 wound on permeable cores mounted on the housing. The stator windings are positioned along two sides of the cylindrical housing 11. Another set of stator field windings 19 are mounted transverse across the arcuate surface of the cylindrical housing 11. The interior of the housing includes a rotary impeller 14 which acts as an armature or rotor as well as an impeller and may have permanent magnets 15 on each end thereof for actuation by the electromagnetic stator field windings 13 and 19. A center shaft 16 mounts to the rotor 14 and the bearing support cups 12 for rotation in the housing 11. Inside the housing 11, as more clearly seen in FIG. 3, are four chambers 1A, 1B, 2A and 2B. Chamber 1A acts as a right atrium and ventricle and fills with blood minus oxygen from the body organs through inlet 20 and which is then pumped by the movement of the rotor 14 from the chamber 1A through the outlet 21 through the right lung picking up oxygen, and back through inlet 22 into chamber 1B. The rotation of the rotor 14 then pushes the blood from the chamber 1B out the outlet 23 back to the body to supply oxygen to the body, while simultaneously blood with reduced oxygen from the body is received through inlet 24 into chamber 2A. The blood in chamber 2A is then pumped by the rotor 14 out outlet 25 through the left lung where it is oxygenated and then through the inlet 26 into chamber 2B. Chamber 2B is pumped by the movement of the rotor through the outlet 27 and back to the body for oxygenating the body. The rotor 14 has a center shaft 16 which is mounted in the hubs 12 as shown in FIG. 1, and is rotated back and forth by the operation of the electromagnets 13 and 19 acting upon the magnets 15. The shaft 16 has a dimple 28 on each end which rides a single ball bearing 30 in the hub 12. The shaft 16 rides in the housing 11 between a pair of arcuate walls 31 and 32 for sealing between the chambers. Each side of the rotor 14 seals between chambers 1A and 2B and, 1B and 2A. The inlets 20 and 22 and the outlets 21 and 23 and the inlets 24 and 26 and the outlets 25 and 27 are connected to their respective chambers through artificial heart valves 33. Each valve has a valve element 34 which seats in a valve seat attached to the walls 35 extending from the arcuate walls 32 and 31 to the housing 11. Each valve element 34 is supported by a valve link 36 pinned with a pin 37 to a bracket 38 and pinned to the valve ring seat with a pin 40. Each valve is actuated to open when the rotor 14 is compressing or expanding the blood in a chamber. Open or closed valves are illustrated in FIGS. 3 and 5. The valves act as check valves to open in only one direction of flow and to close the valve in the opposite direction of flow. As the rotor 14 moves back and forth, chambers 1A and 2A are compressed simultaneously to drive the blood therefrom, while chambers 1B and 2B are expanded pulling blood thereinto. The rotor 14 is then reversed by the electrical circuit to compress the blood in chambers 1B and 2B and to expand chambers 2A and 1A to draw blood back thereinto; thereby, acting first as atriums when drawing in blood and then as ventricles when pumping blood out.

FIG. 6 shows the walls 41 and 42 with the angular wall 41 having a pair of openings with flairs 43 and 44 where tubing attaches to flair and valve and seat are locked into opening, while the wall 42 has a pair of valve openings with flairs 45 and 46 for tubing and valve connection. The walls 42 have a V-shape to allow for larger valves and tubing in the connection of inlet and outlet tubing and valves into each chamber 1A, 2A, 1B and 2B. The flow will not interfere between the valves inasmuch as, one valve in each chamber is always closed when the other valve is open.

Figure 4:
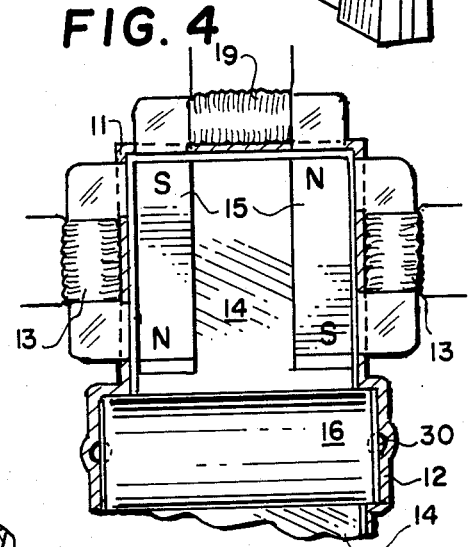
FIG. 4 is a sectional view taken on line 4—4 of FIG. 1.

Referring to FIG. 4, the shaft 16 of the rotor 14 can be seen held in the hub 12 by the two ball bearings 30 for rotation in the housing 11. The rotor impeller 14 has the permanent magnets 15 attached thereto, with the magnets on each side being of opposite polarity. This view shows the electromagnetic stator field windings 13 on either side of the housing 11, and stator windings 19 around the peripheral of the housing 11. The stator windings have a voltage applied thereto controlled by a control circuit for controlling the direction of flow of the electrical current to actuate each stator winding to move the rotor 14 back and forth with a succession of pulses. The stator windings simultaneously are driving both sides of the rotor 14 so that the rotor and impeller react to the magnetic field generated in the stator windings in such a way as to move the rotor back and forth in a sweeping arc to furnish the pumping action within the chambers 1A, 2A, 1B and 2B.

FIG. 7 is a schematic diagram of a timing circuit for driving a magnetic driver in accordance with a schematic diagram of FIG. 8. The magnetic drive circuit in FIG. 8 has each field winding or electromagnet 65 connected between voltage lines 66 and 67 and includes a diode 68 and a transistor driver 70 for actuating each electromagnetic coil 65 in accordance with the timing circuit in FIG. 7. A pair of resistors 71 and 72 are connected across the control electrode of the transistor 70. In FIG. 7, the timing circuit has an oscillator 73 connected to a variable resistor 74 for producing a clock pulse at a pre-determined rate which can be adjusted with the variable resistor 74. The oscillator 73 produces a clocking pulse for the binary up-down counter 75 through a pair of gates 76 and 77. The binary up-down counter 75 is connected to a decoder 79 which produces a pulse to actuate each winding 13 and 19 of FIG. 1 and FIG. 4. The output lines 80 drive the magnets for rotating the rotors 14 in one direction and then in the opposite direction. The decoder 79 has each impulse connected through a pulse generator 81 connected to the gates 76 and 77 operating the timing pulses in conjunction with the oscillator clock 73.

Turning to FIGS. 9 through 12, an alternative embodiment is illustrated which operates with the same flow system, as illustrated in FIGS. 1 through 6, but having a different power-drive system. The artificial heart 90 of FIG. 9 has a casing 92 having a generally cylindrical shape and having a plurality of stator windings 91 on the peripheral edge of the casing 92. The inlets and outlets in this embodiment are the same as illustrated in connection with the embodiment of FIG. 3, with the outlet 93 sends oxygen depleted blood to the right lung for collecting oxygen from the lung prior to the blood being returned through the inlet 94. The inlet 95 receives oxygen deficient blood while the oulet 96 directs the oxygen enhanced blood back to the patient's body. The oulet 97 directs oxygen enhanced blood to the patient's body while the inlet 98 receives oxygen deficient blood from the patient's body. The blood is directed through the outlet 100 to the left lung and returns through the inlet 101. The stator windings 91 have the windings wrapped around soft iron cores 102. In this embodiment a pair of power wheels 103 are mounted on either side of the heart in the housing and contain a plurality of magnets 104 mounted on each power wheel. The power wheels ride freely on bearings 120 A & B on an angular ledge 105 and 106 on either side of the housing. The power wheel 103 also has magnets 108 mounted therein. The magnets 104 are driven by electromagnet stators 91 which then rotate the power wheels on either sde to rotate the magnets 108 attached thereto. The magnets 108 in turn act through the polymer walls 110 to drive the magnets 111 connected to the rotor 107. The rotor rides on a shaft 113 supported by the casing hub 114. The system thus operates similar to a magnetic coupling in which one permanent magnet is controlling the movement and direction of the permanent magnets located inside the artificial heart chambers. The power wheel is rotated back and forth to rotate the rotor inside of the artificial heart in accordance with the driving stator winding being controlled by a circuit in accordance with that shown in FIG. 7.

The rotor for the artificial heart of FIGS. 9 thru 11, is shown in FIG. 12 and it has a shaft 113 aligned by two end bearings 115 held in a dimple 116 in each end of the shaft 113 and having the rotor 107 having the permanent magnets 111 mounted thereto. One purpose of the end bearings or centering balls on the shaft, is to align impeller with housing walls.

FIG. 13 is different from FIGS. 10, 11 and 12 in that the O-ring seals 117 ride in grooves 118 in shaft 113 as seen in FIG. 13, while the power wheel 103 rides on a bearing 120 on inside of angular ledge 106 and is keyed to end of shaft 113 by keys 137. This allows bearing 120 to support the power wheel 103 and shaft 113 at the same time. The outer casing member 121 covers power wheel 103 pressing against centering ball 115 in conjunction with the ball bearing at other end of the shaft for centering of the shaft 113 and impeller 107 in housing 110. A duplicate assembly is shown in place on the left side of FIG. 13, with the rotor impeller 107, which has no magnets, keyed at the ends of the shaft 113 to power wheel 103 riding on bearing 120. The chain of power is transmitted from the stators 91 to power wheel 103 to the keyed shaft 113 to the impeller 107. The power wheel 103 on left side is shown in section in place while the power wheel on the right is a side view of the wheel showing the permanent magnets implanted in the wheel.

Turning to FIGS. 14 thru 17, another power mode of the artificial heart 120 is illustrated having a cylindrical casing 121 with removable walls 122 A & B. The artificial heart of this embodiment has the same chamber configuration as described in connection with FIG. 3, along with the same inlets and outlets. Outlet 122 goes to the right lung while inlet 123 returns from the right lung. Inlet 124 receives blood from the body while outlet 125 directs blood back to the body. Outlet 126 is directed to the body while inlet 127 receives blood from the body. Inlet 128 receives blood from the left lung while outlet 130 directs blood from the artificial heart to the left lung. Each side of the artificial heart in accordance with this embodiment has four fluid lines. Fluid line 131A is directed into a chamber 132 while fluid line 133A is connected into a chamber 134. Chambers 132 and 134 are divided by a power impeller wheel 135A, which is locked to the shaft 136 with keys 137A, so that rotating the rotor plate 135A by the application of fluid into and out of chambers 132 and 134 will rotate the shaft 136 back and forth to rotate the heart impeller rotor 137. The fluid may be air, or alternatively can be a saline solution since the lines 131A and 133A and the chambers 132 and 134 have no connection with the chamber having the impeller rotor 137. A second rotor blade 138A divides a pair of chambers 140 and 141. The chamber 140 is connected by a fluid line 142A while chamber 141 is connected by a fluid line 143A. The chambers are made by the casing walls having the power impeller 135A and 138A placed therein with the annular hub 144A & B sliding over the shaft 136 and connected thereto with keys 137A & B. O-ring seals 145A & B seal the shaft 136 from the interchambers of the artificial heart. Bearings 146A & B allows the power impeller 135A & B to ride thereon while O-ring seals 147A & B and 148A & B seal both sides of the power impeller 135A & B and 138A & B from the leakage of fluid therefrom and the casing wall 150A & B seals the system into the artificial heart. The artificial heart in accordance with this embodiment directs fluid simultaneously in tubes 131A and 143A into chambers 132 and 141 to drive the rotor vanes 135A and 138A, while the tubes 142A and 133A are removing fluid therefrom to pull the vanes 135A and 138A. When the vanes 135A and 138A have been pulled to one side, the fluid flow is reversed in all lines to thereby move vanes 135A and 138A back in the opposite direction. The fluid flow is controlled by a simple pump and a rotating switch valve switching the fluid in accordance with the time of the rotation of the rotary valve. The above is duplicated on opposite sides of FIGS. 14 thru 17 where the assembly is in place.

It should be clear at this point that an artificial heart for pumping blood through a patient's circulatory system has been provided. It should also be clear that the present invention is not to be considered as limited to the embodiments shown which are to be considered illustrative rather than restrictive.

I claim:

1. An artificial heart for pumping blood through a circulatory system comprising in combination:
a housing having a plurality of expandable and contracting chambers formed therein, wherein for each of said plurality of chambers an oscillating impeller forms at least one wall of said chamber;
said oscillating impeller located in said housing and rotably attached thereto for expanding and contracting said housing chambers responsive to an oscillatory movement thereof for which each oscillation consists of a total angular displacement of said impeller of less than 360 degrees;
electromagnetic impeller drive means located outside said housing chamber for rotating said impeller first in one direction and then in said second direction to expand and then to contract a plurality of chambers in said housing, said impeller drive means generating an electromagnetic field through said housing; and
electomagnetic control means for controlling said electronic impeller drive means to move said impeller at a predetermined rate.

2. An artificial heart in accordance with claim 1 in which said housing has four chambers having said impeller forming at least one wall of each chamber whereby rotation of the impeller expands two chambers and contracts two chambers simultaneously.

3. An artificial heart in accordance with claim 2 in which said oscillating impeller is attached to a central shaft supported in said housing.

4. An artificial heart in accordance with claim 3 in which said shaft has an end ball bearing on each end thereof supported in dimples in the end of said shaft and in said housing.

5. An artificial heart in accordance with claim 4 in which said electromagnetic impeller drive means includes a plurality of stator windings.

6. An artificial heart in accordance with claim 5 in which said stator windings are on the outer periphery of said housing.

7. An artificial heart in accordance with claim 6 in which additional stator windings are located on the side walls of said housing.

8. An artificial heart in accordance with claim 7 in which said oscillating impeller has a pair of blades attached to said shaft and each blade has at least one permanent magnet attached thereto.

9. An artificial heart in accordance with claim 8 in which each of the four chambers has an inlet heart valve entering thereinto and an outlet heart valve exiting therefrom to allow blood to be drawn thereinto and pushed therefrom.

10. An artificial heart in accordance with claim 9 in which each said housing chamber has an inlet heart valve on one wall and an exit heart valve on a second wall, and said walls intersect each other.

11. An artificial heart for pumping blood through a circulatory system comprising in combination:
  a housing having four expandable and contracting artificial heart chambers for which an oscillating impeller forms at least one wall of each of said chambers formed therein to which are connected one inlet line and one outlet line entering thereinto for blood to enter and exit each said chamber responsive to the oscillatory rotation of said impeller;
  said oscillating impeller located in said housing and having a pair of blades attached to a central shaft and said central shaft being rotably attached to said housing so that said oscillating impeller can expand and contract each said housing chamber responsive to movement thereof;
  a plurality of auxiliary chambers located in said housing and having at least one power impeller mounted therein and attached to said oscillating impeller shaft;
  a plurality of fluid lines connected to said auxiliary chambers for driving said power impeller to thereby rotate said central shaft and rotate said oscillating impeller to expand and contract said chambers in said housing in such a fashion such that each oscillation of said oscillating impeller consists of a total angular displacement of said impeller of less than 360 degrees whereby said artificial heart expands and contracts the chambers therein responsive to the flow of fluid driving the fluid power impeller.

12. An artificial heart in accordance with claim 11 in which said fluid power impeller has at least two chambers and two fluid pipes connecting thereinto for pushing and pulling said impeller with a fluid to thereby rotate said oscillating impeller.

13. An artificial heart in accordance with claim 12 in which said housing has four auxiliary chambers formed therein and a pair of power impellers each having a pair of blades attached to said central shaft to rotate the shaft responsive to fluid being applied to said auxiliary chambers.

14. An artificial heart in accordance with claim 13 in which said central shaft has a dimple formed at each end thereof and a single ball bearing riding in said dimple and in a dimple formed in said housing for said central shaft to ride thereon.

15. An artificial heart in accordance with claim 14 in which said auxiliary chambers are separated from said artificial heart chambers along said impeller shaft with a plurality of O-ring seals.

16. An artificial heart in accordance with claim 15 in which each said artificial housing chamber has one inlet line and one outlet line entering thereinto for blood to enter and exit each said chamber responsive to the rotation of said oscillating impeller.

* * * * *